(12) United States Patent
McNally et al.

(10) Patent No.: US 10,500,155 B2
(45) Date of Patent: Dec. 10, 2019

(54) LOZENGE DOSAGE FORM HAVING A DISINTEGRATIVE TABLET PORTION AND A CANDY GLASS SHELL PORTION

(71) Applicant: Johnson & Johnson Consumer Inc., Skillman, NJ (US)

(72) Inventors: Gerard P. McNally, Berwyn, PA (US); Gregory Koll, Hillsborough, NJ (US); Oliver Anderson, Glenside, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 15/879,740

(22) Filed: Jan. 25, 2018

(65) Prior Publication Data

US 2018/0333354 A1    Nov. 22, 2018

Related U.S. Application Data

(60) Provisional application No. 62/509,365, filed on May 22, 2017.

(51) Int. Cl.
| | | |
|---|---|---|
| *A61K 9/00* | (2006.01) | |
| *A23G 3/38* | (2006.01) | |
| *A23G 3/54* | (2006.01) | |
| *A61K 9/24* | (2006.01) | |

(52) U.S. Cl.
CPC .............. *A61K 9/0056* (2013.01); *A23G 3/38* (2013.01); *A23G 3/54* (2013.01); *A61K 9/209* (2013.01); *A23V 2002/00* (2013.01); *A23V 2250/5118* (2013.01); *A23V 2250/6422* (2013.01)

(58) Field of Classification Search
CPC ........ A61K 9/0056; A61K 9/209; A23G 3/38; A23G 3/58
See application file for complete search history.

(56) References Cited

U.S. PATENT DOCUMENTS

| | | |
|---|---|---|
| 4,260,596 A | 4/1981 | Mackles |
| 4,517,205 A | 5/1985 | Aldrich |
| 4,851,226 A | 7/1989 | Julian et al. |
| 4,906,478 A | 3/1990 | Valentine et al. |
| 5,075,114 A | 12/1991 | Roche |
| 5,275,822 A | 1/1994 | Valentine et al. |
| 5,302,394 A | 4/1994 | Beahm |
| 5,489,436 A | 2/1996 | Hoy et al. |
| 5,549,906 A | 8/1996 | Santus |
| 5,614,207 A | 3/1997 | Shah et al. |
| 5,616,340 A | 4/1997 | Ells et al. |
| 5,662,920 A | 9/1997 | Santus |
| 5,871,781 A | 2/1999 | Myers et al. |
| 6,024,981 A | 2/2000 | Khankari et al. |

(Continued)

FOREIGN PATENT DOCUMENTS

| | | |
|---|---|---|
| WO | WO 99/47126 A1 | 9/1999 |
| WO | WO 2010/044736 A1 | 4/2010 |
| WO | WO 2013/103318 A1 | 7/2013 |

OTHER PUBLICATIONS

USP 24, 2000 Version, pp. 19-20 and 856 (1999).

(Continued)

*Primary Examiner* — Carlos A Azpuru
(74) *Attorney, Agent, or Firm* — Laura Donnelly

(57) ABSTRACT

The present invention relates to a lozenge dosage form having a disintegrative tablet portion and a candy glass shell portion.

7 Claims, 8 Drawing Sheets

(56) References Cited

U.S. PATENT DOCUMENTS

| | | | |
|---|---|---|---|
| 6,103,260 | A | 8/2000 | Luber et al. |
| 6,106,861 | A | 8/2000 | Chauveau et al. |
| 6,280,761 | B1 | 8/2001 | Santus |
| 8,865,204 | B2 | 10/2014 | Chen et al. |
| 2005/0019376 | A1 | 1/2005 | McNally et al. |
| 2005/0142199 | A1 | 6/2005 | Tian et al. |
| 2005/0238695 | A1 | 10/2005 | Chaudhari et al. |
| 2007/0087053 | A1 | 4/2007 | Hayward |
| 2008/0286340 | A1 | 11/2008 | Andersson et al. |
| 2009/0004248 | A1* | 1/2009 | Bunick ............... A61K 9/0056 424/440 |
| 2009/0011079 | A1 | 1/2009 | Overly, III et al. |
| 2010/0124560 | A1 | 5/2010 | Hugerth |
| 2016/0095818 | A1 | 4/2016 | Hugerth et al. |

OTHER PUBLICATIONS

USP3O-NF25, pp. 276-277.
Lachman, et al. The Theory and Practice of Industrial Pharmacy, Chapter 11, ($3^{rd}$ Edition. 1986). pp. 293-345.
Leiberman et al., "Pharmaceutical Dosage Forms—Tablets", vol. 2, $2^{nd}$ ed., Marcel Dekker Inc., 1990, pp. 213-217 and 327-329.
International Search Report for PCT/US2018/015254 dated Apr. 3, 2018.

\* cited by examiner

LOZENGE DOSAGE FORM HAVING A DISINTEGRATIVE TABLET PORTION AND A CANDY GLASS SHELL PORTION

CROSS REFERENCE TO RELATED APPLICATIONS

This application claims priority of the benefits of U.S. Provisional Application Ser. No. 62/509,365, filed May 22, 2017. The complete disclosure of the aforementioned related U.S. patent application is hereby incorporated by reference for all purposes.

FIELD OF THE INVENTION

The present invention relates to a lozenge dosage form. The present invention also relates to a process for manufacturing the lozenge dosage form and to methods for alleviating symptoms in human subjects upon administration of the lozenge dosage form. The lozenge dosage form, which can comprise one or more therapeutically active agents, is particularly useful in the treatment of cough and cold symptoms, including but not limited to, cough, nasal congestion and sore throat.

BACKGROUND OF THE INVENTION

Pharmaceuticals intended for oral administration are typically provided in solid form as tablets, capsules, pills, lozenges, or granules. Rapidly disintegrative tablets are often employed in the administration of pharmaceuticals where it is impractical to provide a tablet for swallowing whole, for instance with pediatric patients. Several workers in the field have explored rapidly disintegrative tablets (see, e.g., U.S. Pat. Nos. 6,106,861 and 6,024,981 and PCT Application No. WO 99/47126).

A dual portion dosage form that combines the use of a rapidly disintegrative tablet containing a pharmaceutically active agent with a slower disintegrative candy glass shell portion is disclosed. The dosage form provides both the benefit of the fast delivery of pharmaceutically active agent contained within the rapidly disintegrative tablet portion with the benefit of slower degrading candy glass shell portion, which may contain a second pharmaceutically active agent.

The dosage form of the invention can be used to treat, for example, a sore throat, which is characterized by a pain or irritation of the throat or pharynx, usually caused by acute pharyngitis. A sore throat is most often caused by a viral infection. A sore throat can also be caused by a streptococcal infection, tumors, gastroesophageal reflux disease, mononucleosis, and allergies.

A sore throat can develop for many reasons including a viral or bacterial infection, or a common or seasonal allergy. Often associated with an infection, common or seasonal allergy includes some degree of nasal or sinus congestion. This congestion is typically referred to as post-nasal drip, in which mucous originating on the surface of the nasal mucosa or the sinus mucosa drains onto the upper esophagus. The accumulation of nasal mucosa in the upper esophagus also stimulates the swallowing reflex often associated with a sore throat. The swallowing reflex transports the acidic mucous into relatively constant contact with the region of the throat. The acidic nature of the mucous from the sinus mucosa or nasal mucosa erodes the epithelial tissue of the throat thereby exposing the underlying tissue to the acidic mucous. The nerve endings in the underlying tissue in contact with the acidic mucosa cause what one identifies as the discomfort or pain associated with a sore throat. The more inflamed the nasal mucosa or the sinus mucosa, the greater the production of the acidic mucous, the greater the erosion and the greater the severity of the pain and discomfort associated with the sore throat.

The pain of sore throat can be treated with various dosage forms or remedies. Common dosage forms include throat sprays, lozenges, and orally administered tablets or liquids, all of which may contain active ingredients. Sprays and lozenges typically contain topical analgesics or menthol to cool the pain of a sore throat. Orally administered tablets or liquids typically contain systemically acting active ingredients for pain, cough and/or cold; including, e.g., acetaminophen, NSAIDs, decongestants, and/or cough suppressants. In some cases, these products contain sensates for cooling which also help in alleviating pain or providing the perception of alleviating pain.

One of the main disadvantages of such products is lack of immediate effect and/or short duration. In many cases, sprays or liquids do not provide extended pain relief because the composition is swallowed almost immediately upon ingestion.

There remains a need for compositions and methods that are safe and effective to treat, soothe or reduce the severity of a sore throat. Such a composition should work quickly and provide superior sore throat relief for an extended period of time.

U.S. Pat. No. 4,260,596 discloses an edible dosage form having an outer shell and a liquid or gel center which may contain a therapeutically effective amount of a medicament.

U.S. Pat. No. 4,517,205 discloses a co-deposited two-component hard candy having a hard candy shell portion and a core portion which may be soft, and method of making such candy.

U.S. Pat. No. 5,302,394 discloses a process for producing a dextromethorphan medicated hard candy lozenges on a continuous system.

U.S. Pat. Nos. 5,549,906; 5,662,920; and 6,280,761 disclose a nicotine lozenge for smoking cessation.

U.S. Pat. No. 5,614,207 discloses a dry mouth lozenge that comprises a lozenge base, a demulcent, a humectant, and a pharmaceutically acceptable acidulent to stimulate the flow of saliva.

U.S. Pat. No. 5,616,340 discloses a hard-candy based lozenge containing an antacid that is produced in a manner compatible with a continuous process method of manufacture.

U.S. Pat. No. 5,871,781 discloses an apparatus for making comestible units that can include active ingredients and are capable of dissolving in the mouth within several seconds.

U.S. Published Application No. 20050019376 discloses a dosage form that comprises at least one active ingredient, a confectionery composition and at least one face, wherein the relative standard deviation of the weight of the dosage form is less than 1%.

U.S. Published Application No. 20050142199 discloses a pharmaceutical dosage form that comprises a tablet core comprising a pharmaceutically active ingredient and a coating extending over at least 25% of the surface area of the tablet core, the coating resulting from deposition of a powder comprising fusible particles and fusing the particles to form a coating film.

U.S. Published Application No. 20050238695 discloses an organoleptically pleasing lozenge.

U.S. Published Application No. 20070087053 discloses a multi-component composition for the treatment of dry mouth that comprises a first part that rapidly disintegrates in the oral cavity and releases a sialogogic compound, in combination with an effervescent organic acid-based buffering system and a second part that releases a demulcent compound into the oral cavity over a period of several minutes.

U.S. Published Application No. 2008286340 discloses an oral formulation that comprises nicotine and at least one amino acid in an amount effective to buffer the formulation.

U.S. Published Application No. 20090004248 discloses a dosage form including both a disintegrative tablet portion and a hard candy portion, wherein: (i) the disintegrative tablet portion comprises at least one pharmaceutically active agent, and (ii) the hard candy portion covers at least 20% of the surface of the disintegrative tablet portion, and wherein the disintegration time of the hard candy portion is at least ten times longer than the disintegration time of the disintegrative tablet portion. The reference discloses preparation of a dosage form that contains a hard candy portion and a disintegrative tablet portion that includes placing a compressed tablet in a mold that covers the faces of the tablet and injecting a flowable hard candy blend to surround the circumference of the tablet. The reference also discloses preparation of a dosage form that contains two layers that includes placing a compressed tablet on a flat face of a surface of a hard candy that contains PEG 3350; and heating the resulting dosage form such that the PEG 3350 melts and creates adhesion between the surfaces of the tablet and the hard candy.

U.S. Published Application No. 20090011079 discloses a hard-coated confectionary product having a consumable, soft, fortified, high solids and chewy core encapsulated in a hard-consumable coating and a method for making the fortified confectionary.

U.S. Published Application No. 20100124560 discloses a multi portion intra-oral dosage form where at least one portion is rapidly disintegrating and at least one portion is slowly disintegrating, whereby the disintegration time for the slowest disintegrating portion is at least two times longer than for the most rapidly disintegrating portion. The reference discloses preparation of a dual portion dosage form that includes compressing two portions of blended material into tablets by means of direct compression. The reference also discloses preparation of a dual portion dosage form that includes dispensing a melt tablet portion on top of a cooled candy portion.

U.S. Published Applications Nos. WO2013103318 and 20160095818 disclose pharmaceutical dosage forms that comprise a core coated by at least one film coating. The core comprises at least one API, wherein one or more organoleptically disturbing sensations of the active pharmaceutical ingredient (API) are reduced by constituents of the film coating.

U.S. Pat. No. 8,865,204 discloses a lozenge prepared by a process that includes forming a powder blend containing an amorphous carbohydrate polymer into a desired shape and applying radiofrequency energy to the shape for a sufficient period of time to soften or melt the amorphous carbohydrate polymer to fuse the shape into a lozenge product.

There remains a need to produce a lozenge dosage form and an efficient, commercially feasible method of producing such dosage form.

An objective of this invention is to provide an efficient method of producing a two-component dosage form which is readily adaptable to commercial production.

A dosage form can be made, at a commercial production level, having a core portion which is distinctive from the shell portion in function, and, if desired, in texture, flavor, and optical characteristics such as color and light transmission. Moreover, the present invention enables practitioners to conveniently include an active ingredient in an attractive, organoleptically-pleasing, hard candy confection.

SUMMARY OF THE INVENTION

The present invention relates to a dosage form that includes both a disintegrative tablet portion and a candy glass shell portion.

Other features and advantages of the present invention will be apparent from the detailed description of the invention and from the claims.

DETAILED DESCRIPTION OF THE INVENTION

Figure 1:
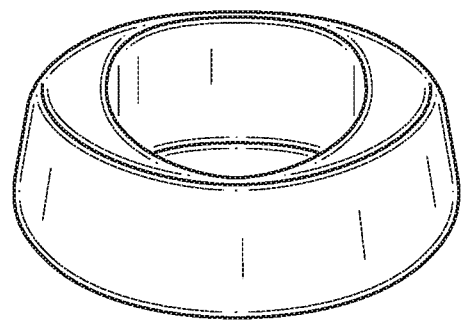
FIGS. 1-8 are photographs of dosage forms made in accordance with the invention.

It is believed that one skilled in the art can, based upon the description herein, utilize the present invention to its fullest extent. The following specific embodiments are to be construed as merely illustrative, and not as limiting the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified. In addition, all ranges set forth herein are meant to include any combinations of values between the two endpoints, inclusively.

As used herein, the term "active", "active agent" or "active ingredient" is used herein in a broad sense and may encompass any material that imparts a therapeutic effect. For example, the active agent or active ingredient can be a pharmaceutical, biologic, nutraceutical, vitamin, dietary supplement, nutrient, herb, foodstuff, dyestuff, nutritional, mineral, supplement, oral care agent or flavoring agent (sensate) or the like and combinations thereof.

"Dosage form" applies to any composition designed to contain a specific pre-determined amount (dose) of a certain ingredient, and for example, an active ingredient as defined herein. Suitable dosage forms may be pharmaceutical drug delivery systems and systems for delivering minerals, vitamins and other nutraceuticals, oral care agents, flavorants, and the like. In a particularly preferred embodiment, the dosage form is an orally administered system for delivering a pharmaceutical active ingredient to the gastro-intestinal tract of a human.

"Rapid disintegration": In one embodiment, the rapidly disintegrative tablet portion meets the criteria for Orally Disintegrating Tablets (ODTs) as defined by the Food and Drug Administration Guidance for Industry, December, 2008. In one embodiment, the rapidly disintegrative tablet portion meets a two-fold definition for orally disintegrating tablets including the following criteria: 1) that the solid tablet is one which contains medicinal substances and which disintegrates rapidly, usually within a matter of seconds, when placed upon the tongue and 2) be considered a solid oral preparation that disintegrates rapidly in the oral cavity, with an in vitro disintegration time of approximately 30 seconds or less, when based on the United States Pharmacopeia (USP 24 NF 29) disintegration test method for the specific medicinal substance or substances.

"Therapeutic effect," means any effect or action of an active ingredient intended to diagnose, treat, cure, mitigate, or prevent disease, or affect the structure or any function of the body.

Suitable sensates that may be used in the invention include menthol, peppermint, mint flavors, fruit flavors, chocolate, vanilla, bubblegum flavors, coffee flavors, liqueur flavors and combinations and the like.

A therapeutically effective amount of active ingredient or ingredients can readily be determined by one skilled in the art.

Disintegrative Tablet Portion

The dosage form of the present invention includes a disintegrative tablet portion. The disintegrative tablet portion includes one or more pharmaceutically active agents and optionally includes one or more compressible excipients, water-swellable excipients, effervescent couples, and other ingredients.

In one embodiment, the disintegrative tablet portion is designed to dissolve in the mouth when placed on the tongue in less than about 60 seconds, e.g., less than about 45 seconds, e.g., less than about 30 seconds, e.g., less than about 15 seconds.

Compressible Excipient

In one embodiment, the disintegrative tablet portion includes one or more compressible excipients. A compressible excipient is an ingredient that can be compressed into a tablet shape without the addition of other binding agents. In one embodiment, the compressible excipient is in the form of a hydrate, and may be selected from organic compounds such as dextrose monohydrate, maltodextrin, lactose monohydrate, and dextrin, as well as inorganic compounds such as dibasic calcium phosphate dihydrate, dibasic sodium phosphate dihydrate, dibasic sodium phosphate heptahydrate, dibasic sodium phosphate dodecahydrate, monobasic sodium phosphate monohydrate, and monobasic sodium phosphate dihydrate. In one embodiment, the disintegrative tablet portion includes a compressible excipient selected from the group consisting of isomalt, dextrose monohydrate, maltodextrin, lactose monohydrate, dextrin, mannitol, maltitol, lactitol, sorbitol, xylitol, erythritol, sucrose, and lactose. In one embodiment, the disintegrative tablet portion includes polyglycitol, a mixture consisting mainly of maltitol and sorbitol and lesser amounts of hydrogenated oligo- and polysaccharides and maltrotriitol. Polyglycitol is also known as hydrogenated starch hydrolysate.

Water-Swellable Excipient

In one embodiment, the disintegrative tablet portion further includes one or more water-swellable excipients. A water swellable excipient is a material that is designed to swell or wick liquid upon contact with a liquid medium and to aid in the disintegration of the compressed tablet. The water-swellable excipient may be selected from superdisintegrants such as crospovidone, croscarmellose, sodium starch glycolate, cellulose compounds such as microcrystalline cellulose, starches, alginic acid and inorganic clays such as bentonite, attapulgite, and magnesium aluminum silicate. In one embodiment, the water-swellable excipient is at least partially hydrated and selected from the group consisting of sodium starch glycolate, crospovidone, croscarmellose, microcrystalline cellulose, starches, hydroxypropyl cellulose, and alginic acid.

Effervescent Couple

In one embodiment, the disintegrative tablet portion further includes one or more effervescent couples. In one embodiment, effervescent couple includes one member selected from the group consisting of sodium bicarbonate, potassium bicarbonate, calcium carbonate, magnesium carbonate, and sodium carbonate; and one member selected from the group consisting of citric acid, malic acid, fumaric acid, tartaric acid, phosphoric acid, and alginic acid.

Poloxamers may be employed. E.g., Lutrol® F 127 is soluble in water, ethanol (95%) and isopropanol. It is insoluble in ether, paraffin and fatty oils. Lutrol F-127 is used primarily as a thickening agent and gel former, but also as a co-emulsifier and consistency enhancer in creams and liquid emulsions. It is also used as a solubilizer for certain active substances such as nifedipine, naproxen and fenticonazole as well as for essential oils in pharmaceutical and cosmetic formulations. Lutrol® F 127 is suitable for the formulation of active substances that show reduced solubility because of neutralization.

Other Ingredients

The disintegrative tablet portion may include other conventional ingredients, including fillers; conventional dry binders, e.g., polyvinyl pyrrolidone; sweeteners such as aspartame, acesulfame potassium, sucralose, and saccharin; lubricants, such as magnesium stearate, stearic acid, talc, and waxes; preservatives; flavors; disintegrants; antioxidants; acidulants, such as citric acid, malic acid, tartaric acid, ascorbic acid, and fumaric acid; surfactants; and coloring agents. The disintegrative tablet portion may include polyethylene glycol (PEG), a polyether compound having the structure H—(O—CH2-CH2)n-OH.

Manufacture

The disintegrative tablet portion may be made in a variety of tableting methods. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. These methods are well known in the art, and are described in detail in, for example, Lachman, et al., The Theory and Practice of Industrial Pharmacy, Chapter 11, (3rd Ed. 1986).

In one embodiment, the disintegrative tablet portion is formed by the direct compression method, which involves directly compacting a blend of pharmaceutically active agent, compressible excipient, water-swellable excipient, and any other appropriate optional ingredients. After blending, a pre-determined volume of particles is filled into a die cavity of a rotary tablet press, which continuously rotates as part of a "die table" from the filling position to a compaction position. The particles are compacted between an upper punch and a lower punch to an ejection position, at which the resulting disintegrative tablet portion is pushed from the die cavity by the lower punch and guided to an ejection chute by a stationary "take-off" bar.

Multiple Layers

In one embodiment, the disintegrative tablet portion has multiple layers each of which include at least one ingredient that is different from the other. In one embodiment, the disintegrative tablet portion contains two layers, wherein the first layer includes a first pharmaceutically active agent and a second layer includes a second pharmaceutically active agent that is different from the first pharmaceutically active agent.

In one embodiment, both the first layer and the second layer are exposed on the surface of the dosage form.

In one embodiment, a first layer of the bi-layered disintegrative tablet portion includes a first flavor and a second layer includes a different second flavor to sequentially deliver a flavor profile.

In one embodiment, the first layer of the bilayer disintegrative tablet portion includes one immediate release active ingredient and the second layer includes an active ingredient which is the same as or different from the first active ingredient and which is delivered in a modified release manner.

Candy Glass Shell Portion

The dosage form of the present invention includes a candy glass shell portion. In one embodiment, the candy glass shell portion includes one or more sugars selected from the group consisting of isomalt, sucrose, lactose, dextrose, corn syrup, lactitol, and lycasin.

In one embodiment, the candy glass shell portion includes a pharmaceutically active agent. In one embodiment, the candy glass shell portion includes a pharmaceutically active agent that is different from the pharmaceutically active agent included within the disintegrative tablet portion.

The candy glass shell portion can be made from a variety of methods including but not limited to uniplast rolling, roping and subsequent cutting and stamping, as well as depositing into molds. These molds can be made from metal, rubber, resin, or plastic.

Compressed sugar lozenges are made via tableting and compression techniques known in the art for making tablets, although they are compressed at hardness levels above those traditionally used for chewable, disintegrative or swallowable tablets, i.e., above about 15 kiloponds, and are designed to dissolve slowly in the oral cavity.

Pharmaceutically Active Agent

The dosage form of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to, antacids such as aluminum-containing active ingredients (e.g., aluminum carbonate, aluminum hydroxide, dihydroxyaluminum sodium carbonate, and aluminum phosphate), bicarbonate-containing active ingredients, bismuth-containing active ingredients (e.g., bismuth aluminate, bismuth carbonate, bismuth subcarbonate, bismuth subgallate, and bismuth subnitrate), calcium-containing active ingredients (e.g., calcium carbonate), glycine, magnesium-containing active ingredients (e.g., magaldrate, magnesium aluminosilicates, magnesium carbonate, magnesium glycinate, magnesium hydroxide, magnesium oxide, and magnesium trisilicate), phosphate-containing active ingredients (e.g., aluminum phosphate and calcium phosphate), potassium-containing active ingredients (e.g., potassium bicarbonate), sodium-containing active ingredients (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole and lansoprazole; gastrointestinal cytoprotectives, such as sucraflate and misoprostol; gastrointestinal prokinetics such as prucalopride; antibiotics for H. pylori, such as clarithromycin, amoxicillin, tetracycline, and metronidazole; antidiarrheals, such as bismuth sub salicylate, kaolin, diphenoxylate, and loperamide; glycopyrrolate; analgesics, such as mesalamine; antiemetics such as ondansetron, cyclizine, diphenyhdroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof; and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as benzydamine, propionic acid derivatives (e.g., ibuprofen, naproxen, ketoprofen, flurbiprofen, fenbufen, fenoprofen, indoprofen, flufprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof; and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof; and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, ambroxol, and guaifenesin; isomers thereof; and pharmaceutically acceptable salts and prodrugs thereof.

Examples of muscle relaxants include, but are not limited to, cyclobenzaprine and chlorzoxazone metaxalone, and orphenadrine, methocarbamol; isomers thereof; and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem; isomers thereof and pharmaceutically acceptable salts and prodrugs thereof.

Examples of appetite suppressants include, but are not limited to, phenylpropanolamine, phentermine, and diethylcathinone; isomers thereof; and pharmaceutically acceptable salts and prodrugs thereof.

Examples of anesthetics (e.g., for the treatment of sore throat) include, but are not limited to dyclonene, benzocaine, and pectin; isomers thereof and pharmaceutically acceptable salts and prodrugs thereof.

Examples of suitable statins include but are not limited to atorvastin, rosuvastatin, fluvastatin, lovastatin, simvustatin, atorvastatin, pravastatin; isomers thereof; and pharmaceutically acceptable salts and prodrugs thereof.

In one embodiment, the pharmaceutically active agent included within the disintegrative tablet portion is selected from phenylephrine, dextromethorphan, ambroxol, pseudoephedrine, acetaminophen, ibuprofen, ketoprofen, loperamide, famotidine, calcium carbonate, simethicone, and menthol; isomers thereof; and pharmaceutically acceptable salts and prodrugs thereof.

In one embodiment, the pharmaceutically active agent included within the candy glass shell portion is selected from phenylephrine, dextromethorphan, ambroxol, pseudoephedrine, chlorpheniramine, methocarbomal, chlophedianol, ascorbic acid, menthol, pectin, dyclonine, and benzocaine; isomers thereof; and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the dosage form in a therapeutically effective amount, which is an amount that produces the desired therapeutic response upon oral administration and can be readily determined by one skilled in the art. In determining such amounts, the pharmaceutically active agent being administered, the bioavailability characteristics of the pharmaceutically active agent, the dose regimen, the age and weight of the patient, and other factors are considered, as is known in the art.

The pharmaceutically active agent may be present in various forms. For example, the pharmaceutically active agent may be dispersed at the molecular level, e.g., melted, within the dosage form, or may be in the form of particles, which in turn may be coated or uncoated. If the pharmaceutically active agent is in form of particles, the particles (whether coated or uncoated) typically have an average particle size of from about 1 to about 2000 microns (e.g., from about 1 to about 1000 microns). In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

If the pharmaceutically active agent has an objectionable taste, the pharmaceutically active agent may be coated with a taste masking coating, as known in the art. Examples of suitable taste masking coatings are described in U.S. Pat. Nos. 4,851,226, 5,075,114, and 5,489,436. Commercially available taste masked pharmaceutically active agents may also be employed. For example, acetaminophen particles which are encapsulated with ethyl cellulose or other polymers by a coaccervation process may be used in the present invention. Coaccervation-encapsulated acetaminophen may be purchased commercially from Eurand America, Inc. (Vandalia, Ohio) or from Circa Inc. (Dayton, Ohio).

The pharmaceutically active agent may be present in pure crystal form or in a granulated form prior to the addition of the coating (e.g., modified release or taste masking coating). Granulation techniques may be used to improve the flow characteristics or particle size of the pharmaceutically active agent to make it more suitable for compression or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation, the details of which are disclosed in, "The Theory and Practice of Industrial Pharmacy, $3^{rd}$ edition", Chapter 11, Lachman, Leon et. al, 1986.

In one embodiment, the pharmaceutically active agent is coated with a combination of a water insoluble film forming polymer (such as but not limited to cellulose acetate or ethylcellulose) and a water-soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent.

In one embodiment, one or more pharmaceutically active ingredients or a portion of the pharmaceutically active ingredient may be bound to an ion exchange resin in the disintegrative tablet portion or the candy glass shell portion for the purposes of taste-masking the pharmaceutically active ingredient or delivering the pharmaceutically active agent in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the disintegrative tablet portion meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999). In another embodiment, the dissolution characteristics of the pharmaceutically active agent are modified, e.g., controlled, sustained, extended, retarded, prolonged, delayed and the like.

Salvation Inducing Agent

In one embodiment, the disintegrative tablet portion, the candy glass shell portion or both include one or more salivation inducing agents. Examples of suitable salivation inducing agents include, but are not limited to, muscarinic acetylcholine receptor agonists (such as pilocarpine and a succulence agent, which is commercially available from International Flavors and Fragrances under the tradename SN12011), binders such as arylalkylamines (e.g., N,N-disubstituted phenylalkylamines wherein the alkyl has from about 1 to about 8 carbons), N,N disubstituted-2-phenylcyclopropylamines, spirooxathiolane-quinnuclidine, Heliopsis longpipes root, and cholinesterase inhibitors. In one embodiment, the disintegrative tablet portion and/or candy glass shell portion includes a salivation inducing agent in an amount from about 0.1% to about 10% by weight of the respective portion.

Dual Portion Dosage Forms

In one embodiment, the candy glass shell portion includes a pharmaceutically active agent different from the pharmaceutically active agent included within the disintegrative tablet portion.

In one embodiment, the dosage form has a multiple layer structure, wherein the disintegrative tablet portion is one layer and the candy glass shell portion is the other layer. In one embodiment, the face of the first layer has a convex shape and the face of the second layer has a concave shape.

In one embodiment, the pharmaceutically active agent included within the disintegrative tablet portion is selected from the group consisting of phenylephrine, dextromethorphan, ambroxol, pseudoephedrine, acetaminophen, ibuprofen, ketoprofen, loperamide, famotidine, calcium carbonate, simethicone, and menthol, and pharmaceutically acceptable salts or prodrugs thereof.

In one embodiment, the pharmaceutically active agent included within the candy glass shell portion is selected from the group consisting of phenylephrine, dextromethorphan, ambroxol, pseudoephedrine, chlorpheniramine, methocarbomal, chlophedianol, ascorbic acid, menthol, pectin, dyclonine, and benzocaine, and pharmaceutically acceptable salts or prodrugs thereof.

Disintegration Test

To determine the disintegration for the candy glass shell portion and the disintegrative tablet portion, the disintegration test for "Uncoated Tablets" according to USP30-NF25 (using water as the immersion fluid) can be used. Briefly, one dosage unit is placed in each of six tubes of a basket, and water (maintained at 37±2 C) is used as the immersion fluid. The disintegration time is determined by taking the average of ten measurements of the time required to completely disintegrate the respective tablet portion. In one embodiment, the disintegration time of the disintegrative tablet portion is less than about 30 sec. In another embodiment, the disintegration time of the disintegrative tablet portion is less than about 15 sec.

Hardness Test

Hardness is a term used in the art to describe the diametral breaking strength as measured by, e.g., a Schleuniger Hardness Tester as described in Leiberman et al., Pharmaceutical Dosage Forms—Tablets, Volume 2, 2nd ed., Marcel Dekker Inc., 1990, pp. 213-217, 327-329. To perform the hardness test, a single tablet is placed into a steel chamber within the hardness tester, and a steel piston pushes against the dosage form until it breaks. The force applied is measured as hardness. In general, 5 tablets are tested from any one sample to provide a mean hardness value in kiloponds.

Sweetness

As used herein, "sweetness index" is a term used to describe the level of sweetness of the disintegrative tablet portion, the candy glass shell portion or the entire dosage form relative to sucrose. Sucrose, defined as the standard, has a sweetness index of 1. For example, the sweetness indices of several known sweetener compounds are listed below:

| Sorbitol | 0.54-0.7 |
|---|---|
| Dextrose | 0.6 |
| Mannitol | 0.7 |
| Sucrose | 1.0 |
| High Fructose Corn Syrup 55% | 1.0 |
| Xylitol | 1.0 |
| Fructose | 1.2-1.7 |
| Cyclamate | 30 |
| Aspartame | 180 |
| Acesulfame K | 200 |
| Saccharin | 300 |
| Sucralose | 600 |
| Talin | 2000-3000 |

In one embodiment, the disintegrative tablet portion and/or candy glass shell portion of the dosage form of the present invention has a sweetness index less than about 0.6. If a higher sweetness is desired, the addition of sweetening agent may increase the sweetness of the dosage form to at least about 0.9, e.g., at least about 1.0, at least about 1.5, or at least about 2.0.

Use of Dosage Form

In one embodiment, the present invention features a method of treating an ailment, the method including orally administering the above described dosage form, wherein the dosage form includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratadine, fexofenadine, diphenhydramine, dextromethorphan, chlorpheniramine, chlophedianol, and pseudoephedrine and the candy glass shell portion includes a pharmaceutically active agent selected from the group of menthol, dyclonine, pectin, and benzocaine.

EXAMPLES

Specific embodiments of the present invention are illustrated by way of the following examples. The invention is not confined to the specific limitations set forth in these examples.

Defining Form

The form of the present invention includes a slow disintegrating candy glass shell portion and a fast disintegrating portion. The candy glass shell portion contains a reservoir that holds the fast disintegrating portion. The fast disintegrating portion has at least one surface which will disintegrate upon contact with a liquid medium. In one embodiment, the fast disintegrating portion is porous.

Hot to Cold

In one embodiment, a porous tablet is formed, the porous tablet is placed in a mold cavity and hot molten candy is deposited on top of the porous tablet.

Cold Plus Hot

In one embodiment, the candy glass shell portion is made in one step and allowed to cool to ambient temperature. In this embodiment, a hot material blend containing the fast disintegrating portion may be added to the candy glass shell portion and allowed to cool to create a single dosage form with two portions.

The hot material blend may be added using several types of processes, including metering or extrusion. Another process for adding the hot material blend would be to create a deformable plug or tablet. The deformable plug would be added to the candy glass shell portion, wherein pressure and/or heat is added to the plug to fill in a predefined space within the candy glass shell portion. The deformable plug could be added either in a hot or cold (ambient) state.

Cold Plus Cold

In one embodiment, the candy glass shell portion is made in one step and allowed to cool to ambient temperature. If the fast disintegrating portion is added to the candy glass shell portion and allowed to adhere, it must be sealed or fit into place. In one embodiment, the deformable plug is added in a cold state, as stated above. In another embodiment, a portion of powder is added to a predefined space or well, and sealed in place. In a version of this embodiment, the fast disintegrating portion contains a meltable material which seals upon cooling and allows the fast disintegrating portion to stay within the predefined space without separation. If it is sealed upon cooling, a heating step can be added after the cold (ambient) mixture is added into the pre-defined space.

Additionally, the fast disintegrating portion may be sealed in place by passing a heating device over its surface. The heating device may be a detached device such as a radiant heater, or a solid contact device such as a conducting scraper bar or a heater conducting roller, which come in direct contact with the dosage form to create a seal on one surface of the fast disintegrating tablet portion. This procedure helps to prevent detachment of the fast disintegrating tablet portion from the candy glass shell portion, while maintaining fast disintegration properties of the fast disintegrating tablet portion.

Examples

The following examples are provided to further illustrate the compositions and methods of the present invention. The present invention is not limited to the examples described.

Example 1: Candy Glass Shell Portion

1. A dye solution containing 10 g purified water, 10 g of hydrogenated starch hydrosylate (Stabilite® SD30[1] and 0.001 g of FD&C Green No. 3[2] was prepared.
2. A candy glass shell portion was prepared as follows. 44.41 g of isomalt (commercially available as galenIQ™ 990[3]) and 5.59 g of the dye solution was heated to 150° C. and mixed and held at 150° C. for 10-15 minutes while missing to boil off the water. The resulting candy glass shell portion was placed into a mold at 140-145° C. and a ⅜-inch metal rod was used to create a reservoir for the fast dissolving portion while the candy glass shell portion was still hot. The candy glass shell portion was allowed to cool. The candy glass shell portion had a solid bottom surface with surrounding side walls and a predefined reservoir.

Example 2: Fast Disintegrating Fill Material Using Xylitol, PEG and Hydrogenated Starch Hydrosylate

TABLE 1

Fill Material for Lozenge

| Material | mg/Tab | % W/W | Batch wt (g) |
|---|---|---|---|
| Xylisorb ® 100DC (xylitol, containing 5% retrograde dextrin)[4], addition A | 16.3 | 8.17 | 4.09 |
| Peppermint Flavor | 4.0 | 2.00 | 1.00 |
| Sucralose NF | 1.3 | 0.67 | 0.34 |
| Polyethylene Glycol 4000 PF[5] | 21.0 | 10.50 | 5.25 |
| Stabilite ® SD30 (Hydrogenated Starch Hydrosylate) | 11.7 | 5.83 | 2.92 |
| Xylisorb ® 100DC (xylitol, containing 5% retrograde dextrin), addition B | 145.7 | 72.83 | 36.42 |
| TOTAL | 200.0 | 100.0 | 50.0 |

[1]Commercially available from Ingredion Incorporated, Bridgewater, NJ. Stabilite ® SD30 is a polyglycitol in a spray-dried form. It is a low sweetness powder that is higher in molecular weight and lower in hygroscopicity than typical polyglycitol products. Typical polyol distribution is as follows: HP1 (sorbitol), 2% d.b.; HP2 (maltitol), 6% d.b.; HP3+, 92% d.b. HP is the degree polyol distribution, lower MW polyol to higher MW polyol. HP1 low MW (sorbitol), HP3 higher MW.
[2]FD&C Green No. 3, CAS No. 2353-45-9, is a bluish green food dye that provides a dark green shade in applications. The color is principally the disodium salt of N-ethyl-N-[4-[[4-[ethyl[(3-sulfophenyl)methyl]amino]phenyl](4-hydroxy-2-sulfophenyl)methylene]-2,5-cyclohexadien-1-ylidene]-3-sulfobenzene-methanaminium hydroxide. It is soluble in water, sparingly soluble in ethanol and insoluble in vegetable oils.
[3]Commercially available from the Beneo GmbH. galenIQ ™ 990 is a pharmaceutical graded isomalt for high-boiled lozenge applications. Properties include solubility 25 g/100 g solution at 20° C. in water; narrow particle size distribution; high chemical and temperature stability; low hygroscopicity - reduced adsorption of moisture; and high glass-transition temperature.
[4]Commercially available from Roquette America, Inc. XYLISORB ® is Roquette's trade name for a range of xylitol powders that can be used in a variety of pharmaceutical and cosmetic formulations. Xylisorb 100DC. 100 micron, also contains 5% dextrins.
[5]PEG 4000 PF. Micronized PEG from Clariant.

Part A: Procedure for Mixing and Heating Materials (using the Formula in Table 1)

1. The materials from Table 1 were added to a vessel capable of heating. Xylisorb® 100DC addition A and Xylisorb® addition B were added separately at different times.
2. The materials were heated to 90° C., at which point the xylitol melted indicating that this would not be the most desirable process material for creating a fast dissolving portion. The lower melting point of the xylitol used in this example was not conducive to this procedure. This form of xylitol may work as a base fill material if used with a lower temperature process, for instance, if placed in the candy shell portion cold and treated only with surface heat.

Example 3: Fast Disintegrating Fill Material Using Maltitol, PEG and Maltodextrin

TABLE 2

Fill Material for Lozenge

| Material | mg/Tab | % W/W | Batch wt (g) |
|---|---|---|---|
| Maltitol (SweetPearl ® P90)[6], addition A | 16.3 | 8.17 | 4.09 |
| Peppermint Flavor | 4.0 | 2.00 | 1.00 |
| Sucralose | 1.3 | 0.67 | 0.34 |
| Polyethylene Glycol 4000PF | 21.0 | 10.50 | 5.25 |
| Maltitol (SweetPearl ® P90), addition B | 145.7 | 72.83 | 38.42 |
| Maltrin ® QD M500 (Maltodextrin)[7] | 11.7 | 5.83 | 2.92 |
| TOTAL | 200.0 | 100.0 | 50.0 |

[6]Commercially available from Roquette America, Inc. SweetPearl ® P90 is a fine particle size bulk sweetener produced from naturally-occurring compounds in wheat and maize. SweetPearl ® is the maltitol by Roquette, and is often used in baked goods and chocolate.
[7]Commercially available from Grain Processing Corporation, Muscatine, Iowa. MALTRIN QD ® (quickly dispersible) maltodextrins are bland, minimally sweet, white, free-flowing carbohydrate powders that have a high rate of dissolution and excellent particulate strength, produced from corn of U.S. origin. They are products with varying length polymer profiles that provide a wide range of viscosity and solubility characteristics. STANDARD SPECIFICATIONS: Dextrose Equivalent 9.0-12.0; Moisture, % 6.0 max.; Ash (sulfated), % 0.5 max.; pH (20% solution) 4.0-5.1; Bulk Density (packed), lb/cu ft 16.0-24.0; Particle Size, % through; 20 mesh 90.0 min.; 200 mesh 10.0 max.; Aerobic Plate Count, CFU/g; 100 max.; Yeast/Mold, CFU/g 100 max.; E. coli Negative/10 g; Salmonella Negative/25 g; CARBOHYDRATE LABELING INFORMATION: DP1 (glucose) grams per 100 grams 1; DP2 (maltose) grams per 100 grams 3; ** Carbohydrate information reported "as is". DEGREE OF POLYMERIZATION (DP PROFILE): DP1-7, % 30; DP8-25, % 35; DP26-40, % 1; Greater than DP40, % 34.

Part A: Procedure for Mixing and Heating Materials
The materials in Table 2 were combined as follows:
1. The first portion (addition A) of maltitol, flavor and sucralose were blended in a vessel
2. The second portion (addition B) of maltitol, polyethylene glycol and blend from step one were added to a plastic bag and mixed end-over-end for 2 minutes.
3. The maltodextrin was added to the plastic bag and mixed end-over-end for 2 minutes.
4. The total mixture was heated to 90° C. while manually mixing on a hot plate.
5. The heated mixture was transferred to the candy glass shell portion from Example 1 with slight compression on the top surface and allowed to cool in place. This fill had enough cohesive strength to stay in the candy glass shell portion of the dosage form.

Example 4: Fast Disintegrating Fill Material Using Maltitol, PEG and Starch

TABLE 3

Fill Material Formulation for Lozenge

| Material | mg/Tab | % W/W | Batch wt (g) |
|---|---|---|---|
| Maltitol (SweetPearl ® P90), addition A | 16.3 | 8.17 | 4.09 |
| Peppermint Flavor | 4.0 | 2.00 | 1.00 |
| Sucralose NF | 1.3 | 0.67 | 0.34 |
| Polyethylene Glycol 4000PF | 21.0 | 10.50 | 5.25 |
| Maltitol (SweetPear ®l P90)[a,] addition B | 145.7 | 72.83 | 38.42 |
| Ultrasperse ® M Starch[8] | 11.7 | 5.83 | 2.92 |
| TOTAL | 200.0 | 100.0 | 50.0 |

[8]Commercially available from Ingredion Incorporated, Bridgewater, NJ. ULTRA-SPERSE M modified food starch is a high performance, cold water swelling (CWS) starch derived from waxy maize It exhibits excellent dispersibility and imparts superior sheen, clarity, and smoothness when compared to traditional pre-gelatinized starches.

Part A: Procedure for Mixing and Heating Materials
The materials in Table 3 were combined as follows:
1. The first portion (addition A) of maltitol, flavor and sucralose were blended in a vessel.
2. The second portion (addition B) of maltitol, polyethylene glycol and blend from step one were added to a plastic bag and mixed end-over-end for 2 minutes.
3. The Ultrasperse® M starch was added to the plastic bag and mixed end-over-end for 2 minutes.
4. The total mixture was heated to 90° C. while manually mixing on a hot plate.
5. The heated mixture was transferred to the candy glass shell portion form from Example 1 with slight compression on top surface and allowed to cool in place. This mixture produced a smooth texture.

Example 5: Fast Disintegrating Fill Material Using Maltitol, Poloxamer and Starch

TABLE 4

Fill Material for Lozenge

| Material | mg/Tab | % W/W | Batch wt (g) |
|---|---|---|---|
| Maltitol (SweetPearl ® P90), addition A | 16.3 | 8.17 | 4.09 |
| Peppermint Flavor | 4.0 | 2.00 | 1.00 |
| Sucralose | 1.3 | 0.67 | 0.34 |
| Lutrol micro 127 MP[9] | 21.0 | 10.50 | 5.25 |
| Maltitol (SweetPear ®l P90), addition B | 145.7 | 72.83 | 38.42 |
| Ultrasperse ® M Starch | 11.7 | 5.83 | 2.92 |
| TOTAL | 200.0 | 100.0 | 50.0 |

[9]Commercially available from BASF North America. The Lutrol F block co-polymers are synthetic co-polymers of ethylene oxide and propylene oxide represented by the following chemical structure:

Part A: Procedure for Mixing and Heating materials (using the Formula in Table 4)

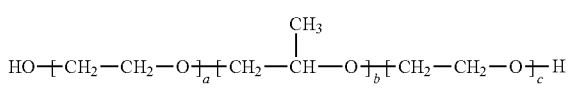

The poloxamer is 407, a is 101 and b is 56.
The materials in Table 4 were combined as follows:
1. The first portion (addition A) of maltitol, flavor and sucralose were blended in a vessel.

2. The second portion (addition B) of maltitol, Lutrol and blend from step one were added to a plastic bag and mixed end-over-end for 2 minutes.
3. The Ultrasperse® M starch was added to the plastic bag and mixed end-over-end for 2 minutes.
4. The total mixture was heated to 90° C. while manually mixing on a hot plate.
5. The heated mixture was transferred to the candy glass shell portion form from Example 1 with slight compression on top surface and allowed to cool in place. This fill material was more brittle than formulas using polyethylene glycol, and susceptible to falling out of the mold. Lutrol was used in this example to replace polyethylene glycol, but it did not provide enough cohesive strength.

Example 6: Fast Disintegrating Fill Material Using Hydrogenated Starch Hydrosylate and PEG

TABLE 5

Fill Material for Lozenge

| Material | mg/Tab | % W/W | Batch wt (g) |
|---|---|---|---|
| Hydrogenated Starch Hydrosylate (Stabilite SD 30), addition A | 20.0 | 10.00 | 5.00 |
| Peppermint Flavor | 4.0 | 2.00 | 1.00 |
| Sucralose, NF | 1.3 | 0.67 | 0.34 |
| Polyethylene Glycol 4000 PF | 30.0 | 15.00 | 7.50 |
| Hydrogenated Starch Hydrosylate (Stabilite SD 30), addition B | 144.7 | 72.33 | 36.17 |
| TOTAL | 200.0 | 100.0 | 50.0 |

Part A: Procedure for Mixing and Heating materials (Using the Formula in Table 5)
The materials in Table 5 were combined as follows:
1. The first portion of hydrogenated starch hydrosylate (addition A), flavor and sucralose were blended in a vessel
2. The second portion of hydrogenated starch hydrosylate (addition B) and blend from step one were added to a plastic bag and mixed end-over-end for 2 minutes.
3. The polyethylene glycol was added to the plastic bag and mixed end-over-end for 2 minutes.
4. The total mixture was heated to 90° C. while manually mixing on a hot plate.
5. The heated mixture was transferred to the candy glass shell portion from Example 1 with slight compression on top surface and allowed to cool in place. This fill material was more brittle than formulas using maltitol, and susceptible to falling out of the mold. Even though this fill material was tamped with some pressure, it did not provide enough cohesive strength.

Example 7: Fast Disintegrating Fill Material Using Erythritol and PEG

TABLE 6

Fill Material Formulation for Lozenge

| Material | mg/Tab | % W/W | Batch wt (g) |
|---|---|---|---|
| Erythritol (Erylite ®)[10], addition A | 20.0 | 10.00 | 5.00 |
| Peppermint Flavor | 4.0 | 2.00 | 1.00 |
| Sucralose, NF | 1.3 | 0.67 | 0.34 |
| Polyethylene Glycol 4000 PF | 30.0 | 15.00 | 7.50 |
| Erythritol (Erylite ®) powder, addition B | 144.7 | 72.33 | 36.17 |
| TOTAL | 200.0 | 100.0 | 50.0 |

[10]Commercially available from Jungbunzlauer Suisse AG, Basel, Switzerland. ERYLITE ®, CAS Registry No. 149-32-6, is a bulk sweetener with a caloric value close to zero. Chemically, it is a four-carbon sugar alcohol (polyol). ERYLITE ® is produced by microbial fermentation of a carbohydrate substrate. ERYLITE is a white odourless crystalline material or powder of high purity. ERYLITE occurs naturally in a wide variety of foods, including many fruits and mushrooms, as well as in fermented foods such as cheese, wine, beer, and soy sauce. Its sweetening profile is very close to sucrose, while its sweetness amounts up to 60-70% of the sweetness of sucrose.

Part A: Procedure for Mixing and Heating materials (using the Formula in Table 6)
The materials in Table 6 were combined as follows:
1. The first portion (addition A) of erythritol, flavor and sucralose were blended in a vessel.
2. The second portion (addition B) of erythritol and blend from step one were added to a plastic bag and mixed end-over-end for 2 minutes.
3. The polyethylene glycol was added to the plastic bag and mixed end-over-end for 2 minutes.
4. The total mixture was heated to 90° C. while manually mixing on a hot plate.
5. The heated mixture was transferred to the candy glass shell portion form from Example 1 with slight compression on top surface and allowed to cool in place. This fill had better strength and disintegration characteristics and had a smoother texture than maltitol due to the smaller particle size. The strength allowed it to stay in the candy glass shell portion. A smaller particle size of maltitol may also have similar texture.

Example 8: Fast Disintegrating Fill Material Using Erythritol, Xylitol and Nicotine

TABLE 7

Fill Material Formulation for Lozenge

| Material | mg/Tab | % W/W | Batch wt (g) |
|---|---|---|---|
| Erythritol (Erylite ®) powder, addition A | 23.70 | 78.985 | 118.48 |
| Xylisorb ® 300[11] | 3.00 | 10.00 | 15.00 |
| Nicotine Ditartrate Dihydrate (Siegfried AG) | 3.00 | 10.00 | 15.00 |
| Titanium Dioxide | 0.30 | 1.00 | 1.50 |
| FD&C Blue #1, Al Lake | 0.00 | 0.015 | 0.0225 |
| TOTAL | 200.0 | 100.0 | 150.0 | a: Commercially available from Jungbunzlauer Suisse AG

Part A: Procedure for Mixing and Heating materials (using the Formula in Table 7)
The materials in Table 7 were combined as follows:
1. The first portion (addition A) of erythritol, Xylisorb, titanium dioxide and FD&C Blue #1 were blended in a vessel.
2. The nicotine ditartrate dihydrate was added and blended manually.
3. The total mixture was heated to 90° C. while manually mixing on a hot plate.

4. The heated mixture was transferred to the candy glass shell portion form from Example 1 with slight compression on top surface and allowed to cool in place.

Example 9: Fast Disintegrating Fill Material Using Maltitol, PEG and Hydrogenated Starch Hydrosylate

TABLE 8

Fill Material Formulation for Lozenge

| Material | mg/Tab | % W/W | Batch wt (g) |
|---|---|---|---|
| Maltitol (SweetPearl ® P90), addition A | 16.3 | 8.17 | 4.09 |
| Peppermint Flavor | 4.0 | 2.00 | 1.00 |
| Sucralose | 1.3 | 0.67 | 0.34 |
| Polyethylene Glycol 4000 | 21.0 | 10.50 | 5.25 |
| Maltitol (SweetPear ®l P90)[a,] addition B | 145.7 | 72.83 | 38.42 |
| Stabilite ® SD 30 (Hydrogenated Starch Hydrosylate) | 11.7 | 5.83 | 2.92 |
| TOTAL | 200.0 | 100.0 | 50.0 |

[1]Commercially available from Roquette. XYLISORB ® is Roquette's trade name for a range of xylitol powders that can be used in a variety of pharmaceutical and cosmetic formulations. XYLISORB ® 300 particles have a mean diameter of 300 µm.

Part A: Procedure for Mixing and Heating materials
The materials in Table 8 were combined as follows:
1. The first portion of maltitol (addition A), flavor and sucralose were blended in a vessel.
2. The second portion of maltitol (addition B), polyethylene glycol and blend from step one were added to a plastic bag and mixed end-over-end for 2 minutes.
3. The hydrogenated starch hydrosylate was added to the plastic bag and mixed end-over-end for 2 minutes.
4. The total mixture was heated to 90° C. while manually mixing on a hot plate.
5. The heated mixture was transferred to the candy glass shell portion form from Example 1 with slight compression on top surface and allowed to cool in place. The hard mass stayed in the dosage form without falling out.

Example 10: Fast Disintegrating Fill Material Using Xylitol, Poloxamer and Starch

TABLE 8

Fill Material Formulation for Lozenge

| Material | mg/Tab | % W/W | Batch wt (g) |
|---|---|---|---|
| Xylisorb ® 300 (crystalline), addition A | 16.3 | 8.17 | 4.09 |
| Peppermint Flavor | 4.0 | 2.00 | 1.00 |
| Sucralose | 1.3 | 0.67 | 0.34 |
| Polyethylene Glycol 4000 | 21.0 | 10.50 | 5.25 |
| Lutrol 127 MP | 5.0 | 2.50 | 1.25 |
| Xylisorb 300 (crystalline), addition B | 140.7 | 70.33 | 35.17 |
| Ultrasperse ® Starch | 11.7 | 5.83 | 2.92 |
| TOTAL | 200.0 | 100.0 | 50.0 |

Part A: Procedure for Mixing and Heating materials (using the Formula in Table 8)
The materials in Table 8 were combined as follows:
1. The first portion of Xylisorb® (addition A), flavor and sucralose were blended in a vessel.
2. The second portion of Xylisorb® (addition B), polyethylene glycol, Lutrol and blend from step one were added to a plastic bag and mixed end-over-end for 2 minutes.
3. The Ultrasperse was added to the plastic bag and mixed end-over-end for 2 minutes.
4. The total mixture was heated to 90° C. while manually mixing on a hot plate.
5. The heated mixture was transferred to the candy glass shell portion form from Example 1 with slight compression on top surface and allowed to cool in place. The hard mass stayed in the dosage form without falling out.

The foregoing examples are not intended to limit the scope of the present invention, which may be set out in the claims. In particular, various equivalents and substitutions will be recognized by those skilled in the art in view of the foregoing disclosure and these are contemplated to be within the scope of the invention.

Figure 2:
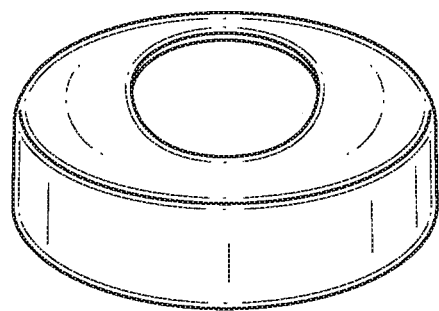
Figure 3:
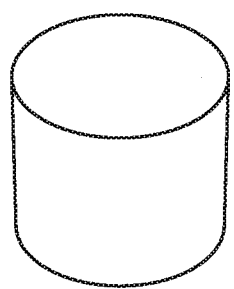
Figure 4:
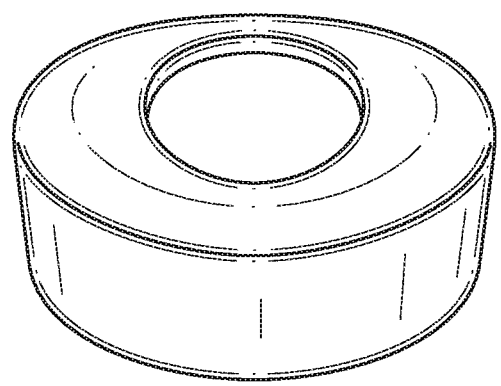
Figure 5:
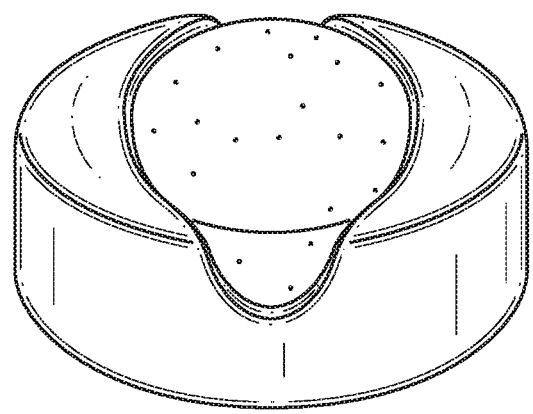
Figure 6:
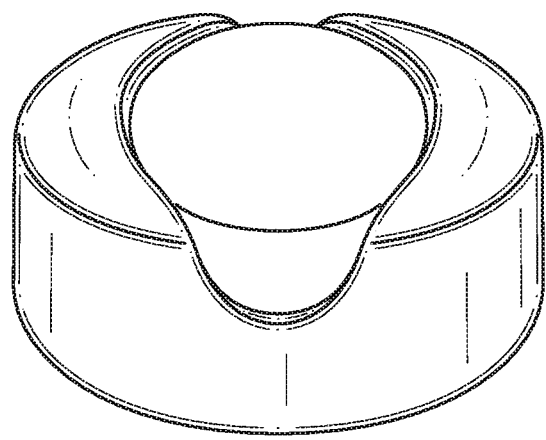
Figure 7:
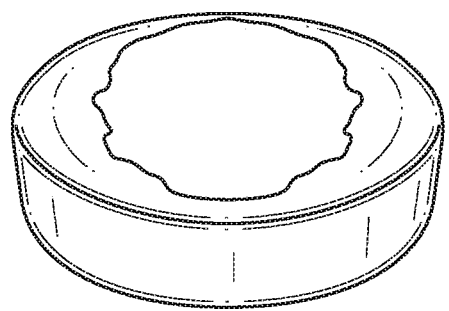
Figure 8:
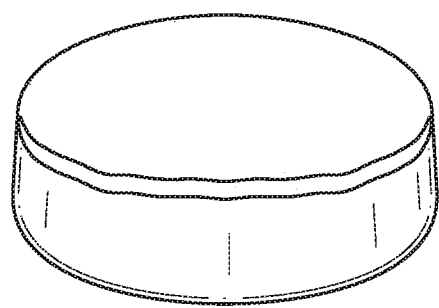

The invention claimed is:

1. A lozenge dosage form comprising:
   a disintegrative tablet portion; and
   a candy glass shell portion;
   wherein the disintegrative tablet portion comprises at least one pharmaceutically active ingredient;
   wherein the disintegrative tablet portion has a form of a plug as depicted in FIG. 3;
   wherein the plug is added to the candy glass shell portion after the candy glass shell portion is formed;
   wherein pressure and/or heat is added to the plug to fill in a predefined space within the candy glass shell portion;
   wherein the candy glass shell portion has a form of a spherical cap as depicted in FIG. 1; and
   wherein when combined the disintegrative tablet portion and the candy glass shell portion have a form as depicted in FIG. 2.

2. The lozenge dosage form of claim 1, wherein the candy glass shell portion comprises at least one pharmaceutically active ingredient.

3. The lozenge dosage form of claim 1, wherein the disintegrative tablet portion comprises at least two excipients selected from the group consisting of a poloxamer, polyethylene glycol, a sugar, a starch and a starch hydrosylate.

4. The lozenge dosage form of claim 1, wherein the disintegrative tablet portion comprises multiple layers.

5. The lozenge dosage form of claim 4, wherein the disintegrative tablet portion comprises two layers, wherein a first layer comprises a first pharmaceutically active ingredient, and wherein a second layer comprises a second pharmaceutically active ingredient.

6. The lozenge dosage form of claim 5, wherein the first layer and the second layer are exposed on a surface of the dosage form.

7. A method of treating an ailment comprising orally administering the lozenge dosage form of claim 1.

\* \* \* \* \*